(12) United States Patent
Stadler et al.

(10) Patent No.: US 9,480,844 B2
(45) Date of Patent: Nov. 1, 2016

(54) METHOD AND APPARATUS FOR REDUCING NOISE IN A MEDICAL DEVICE

(75) Inventors: Robert W. Stadler, Shoreview, MN (US); Richard P. M. Houben, Lanaken (BE); Tim Dirk Jan Jongen, Heerlen (NL)

(73) Assignee: Medtronic, Inc., Minneapolis, MN (US)

( * ) Notice: Subject to any disclaimer, the term of this patent is extended or adjusted under 35 U.S.C. 154(b) by 281 days.

(21) Appl. No.: 12/915,093

(22) Filed: Oct. 29, 2010

(65) Prior Publication Data

US 2012/0108990 A1    May 3, 2012

(51) Int. Cl.
*A61N 1/37* (2006.01)
*A61N 1/36* (2006.01)
*A61N 1/362* (2006.01)

(52) U.S. Cl.
CPC ........... *A61N 1/3702* (2013.01); *A61N 1/3621* (2013.01)

(58) Field of Classification Search
CPC ........ A61N 1/36; A61N 1/3621; A61N 1/37; A61N 1/3702
USPC ............. 600/509, 510, 515; 607/2, 9, 27, 28
See application file for complete search history.

(56) References Cited

U.S. PATENT DOCUMENTS

| | | | |
|---|---|---|---|
| 4,374,382 A | 2/1983 | Markowitz | |
| 4,417,306 A * | 11/1983 | Citron | A61B 5/04325 600/516 |
| 4,428,378 A | 1/1984 | Anderson et al. | |
| 5,010,887 A * | 4/1991 | Thornander | 600/509 |
| 5,107,833 A | 4/1992 | Barsness | |
| 5,117,824 A | 6/1992 | Keimel et al. | |
| 5,168,871 A | 12/1992 | Grevious | |
| 5,292,343 A | 3/1994 | Blanchette et al. | |
| 5,314,450 A | 5/1994 | Thompson | |
| 5,324,315 A | 6/1994 | Grevious | |
| 5,348,008 A * | 9/1994 | Bornn et al. | 600/301 |
| 5,354,319 A | 10/1994 | Wyborny et al. | |
| 5,365,932 A * | 11/1994 | Greenhut | 600/508 |
| 5,383,909 A | 1/1995 | Keimel | |
| 5,545,186 A | 8/1996 | Olson et al. | |
| 5,564,430 A * | 10/1996 | Jacobson et al. | 600/510 |
| 5,620,472 A * | 4/1997 | Rahbari | 607/27 |
| 5,755,736 A | 5/1998 | Gillberg et al. | |
| 6,112,119 A * | 8/2000 | Schuelke et al. | 607/9 |
| 6,230,059 B1 * | 5/2001 | Duffin | 607/60 |
| 6,477,406 B1 * | 11/2002 | Turcott | 600/518 |
| 8,005,539 B2 * | 8/2011 | Burnes et al. | 607/2 |

(Continued)

OTHER PUBLICATIONS (PCT/US2011/058033) PCT Notification of Transmittal of the International Search Report and the Written Opinion of the International Searching Authority.

*Primary Examiner* — Christopher A Flory

(57) ABSTRACT

A method and apparatus for detecting a cardiac event in a medical device that includes sensing a cardiac signal, detecting a cardiac event in response to the sensed signal, determining whether an interval associated with the cardiac signal is less than an interval threshold, determining a noise metric in response to an interval associated with the cardiac signal being less than the interval threshold, determining whether the noise metric is greater than a noise metric threshold, and determining whether to inhibit detecting in response to determining whether an interval associated with the cardiac signal is less than the interval threshold and determining whether the noise metric is greater than the noise metric threshold.

22 Claims, 6 Drawing Sheets

(56) References Cited

U.S. PATENT DOCUMENTS

| | | | |
|---|---|---|---|
| 2004/0106957 A1* | 6/2004 | Palreddy et al. | 607/9 |
| 2005/0038351 A1* | 2/2005 | Starobin | A61B 5/0456 |
| | | | 600/516 |
| 2005/0187585 A1* | 8/2005 | Mussig | A61N 1/3622 |
| | | | 607/9 |
| 2007/0232945 A1* | 10/2007 | Kleckner et al. | 600/509 |
| 2007/0239050 A1* | 10/2007 | Ghanem et al. | 600/512 |
| 2007/0270704 A1* | 11/2007 | Ghanem et al. | 600/521 |
| 2008/0275516 A1 | 11/2008 | Ghanem | |
| 2008/0275517 A1* | 11/2008 | Ghanem et al. | 607/9 |
| 2008/0275518 A1* | 11/2008 | Ghanem et al. | 607/17 |
| 2008/0275519 A1* | 11/2008 | Ghanem et al. | 607/17 |
| 2009/0082682 A1* | 3/2009 | Fischell | A61B 5/0006 |
| | | | 600/509 |
| 2009/0299429 A1 | 12/2009 | Mayotte | |
| 2010/0099995 A1* | 4/2010 | Lian | A61N 1/3702 |
| | | | 600/515 |
| 2010/0106209 A1 | 4/2010 | Gunderson | |
| 2010/0114208 A1* | 5/2010 | Donofrio et al. | 607/5 |
| 2010/0114224 A1* | 5/2010 | Krause et al. | 607/8 |
| 2010/0152595 A1* | 6/2010 | Skinner | A61B 5/02405 |
| | | | 600/509 |
| 2010/0204597 A1* | 8/2010 | Ghanem et al. | 600/512 |
| 2011/0270102 A1* | 11/2011 | Zhang et al. | 600/512 |
| 2011/0270109 A1* | 11/2011 | Zhang et al. | 600/518 |
| 2011/0270110 A1* | 11/2011 | Zhang et al. | 600/518 |
| 2011/0270333 A1* | 11/2011 | Stadler et al. | 607/4 |
| 2011/0270334 A1* | 11/2011 | Stadler et al. | 607/4 |
| 2011/0270335 A1* | 11/2011 | Stadler et al. | 607/5 |
| 2012/0108992 A1* | 5/2012 | Patel | A61B 5/04023 |
| | | | 600/509 |
| 2012/0108994 A1* | 5/2012 | Patel | A61B 5/04023 |
| | | | 600/515 |

* cited by examiner

METHOD AND APPARATUS FOR REDUCING NOISE IN A MEDICAL DEVICE

TECHNICAL FIELD

This disclosure relates generally to detection of cardiac events in a medical device and, in particular, to a method and apparatus for reducing effects of noise on detection of cardiac events in a medical device.

BACKGROUND

A variety of medical devices for delivering a therapy and/or monitoring a physiological condition have been used clinically or proposed for clinical use in patients. Examples include medical devices that deliver therapy to and/or monitor conditions associated with the heart, muscle, nerve, brain, stomach or other organs or tissues. In some medical devices, one or more elongated electrical leads are utilized that carry electrodes for one or both sensing intrinsic electrical signals within the patient and delivering therapeutic electrical signals to certain organs or tissues, and/or other sensors for sensing physiological parameters of a patient. In other medical devices, the electrodes and/or sensors are formed on or located within a housing of the device, rather than being positioned on an electrode lead.

During detection of cardiac events, the observed electrical signal of cardiac activity can be corrupted by noise and/or artifacts from a large variety of sources. The highly constrained computational capability of these devices limits the available options for noise recognition and rejection algorithms. Therefore, what is needed is a method and apparatus for reducing the effect of noise during detection of a cardiac event and that minimizes computational demand on the medical device.

BRIEF DESCRIPTION OF THE DRAWINGS

Aspects and features of the present disclosure will be appreciated as the same becomes better understood by reference to the following detailed description of the embodiments of the invention when considered in connection with the accompanying drawings, wherein.

DETAILED DESCRIPTION

In the following description, references are made to illustrative embodiments. It is understood that other embodiments may be utilized without departing from the scope of the disclosure.

Figure 1:
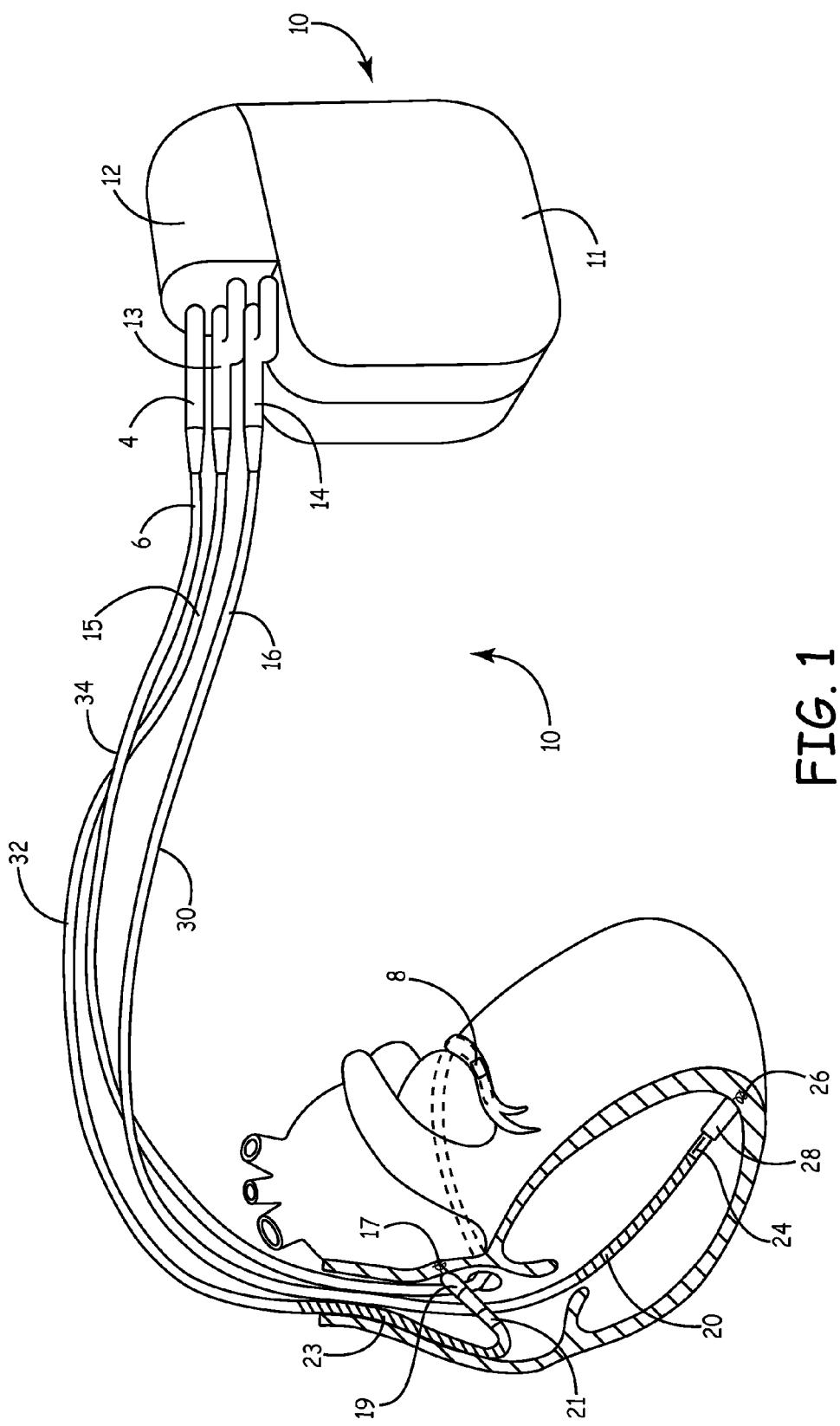
FIG. 1 is a schematic representation of an exemplary medical device in which the method and apparatus of the present application may be implemented.

FIG. 1 is a schematic representation of an exemplary medical device in which the method and apparatus of the present application may be implemented. As illustrated in FIG. 1, a medical device according to the present disclosure may be in the form of an implantable pacemaker/cardioverter/defibrillator 10 that includes a ventricular lead 30, an atrial/superior vena cava (SVC) lead 32, and a coronary sinus lead 34.

Ventricular lead 30 includes an elongated insulative lead body 16, carrying three mutually insulated conductors. Located adjacent the distal end of ventricular lead 30 are a ring electrode 24, an extendable helix electrode 26, mounted retractably within an insulative electrode head 28, and an elongated coil electrode 20. Each of the electrodes is coupled to one of the conductors within the lead body 16. Electrodes 24 and 26 are employed for cardiac pacing and for sensing ventricular depolarizations. At the proximal end of ventricular lead 30 is a bifurcated connector 14 that carries three electrical connectors, each coupled to one of the coiled conductors.

Atrial/SVC lead 32 includes an elongated insulative lead body 15, also carrying three mutually insulated conductors. A ring electrode 21 and an extendible helix electrode 17, mounted retractably within an insulative electrode head 19, are located adjacent the J-shaped distal end of atrial/SVC lead 32. Each of the electrodes is coupled to one of the conductors within the lead body 15. Electrodes 17 and 21 are employed for atrial pacing and for sensing atrial depolarizations. An elongated coil electrode 23 is provided, proximal to electrode 21 and coupled to the third conductor within the lead body 15. At the proximal end of the lead is a bifurcated connector 13 that carries three electrical connectors, each coupled to one of the coiled conductors.

Coronary sinus lead 34 includes an elongated insulative lead body 6, carrying one conductor, coupled to an elongated coiled defibrillation electrode 8. Electrode 8, illustrated in broken outline, is located within the coronary sinus and great vein of the heart. At the proximal end of coronary sinus lead 34 is a connector plug 4, which carries an electrical connector, coupled to the coiled conductor.

Pacemaker/cardioverter/defibrillator 10 includes a hermetic enclosure 11 containing the electronic circuitry used for generating cardiac pacing pulses for delivering cardioversion and defibrillation shocks and for monitoring the patient's heart rhythm. Pacemaker/cardioverter/defibrillator 10 is shown with the lead connector assemblies 4, 13 and 14 inserted into the connector block 12, which serves as a receptacle and electrical connector for receiving the connectors, 4, 13 and 14 and interconnecting the leads to the circuitry within enclosure 11.

Optionally, insulation of the outward facing portion of the housing 11 of the pacemaker/cardioverter/defibrillator 10 may be provided or the outward facing portion may instead be left uninsulated, or some other division between insulated and uninsulated portions may be employed. The uninsulated portion of the housing 11 optionally serves as a subcutaneous defibrillation electrode, used to defibrillate either the atria or ventricles. Other lead configurations and electrode locations may of course be substituted for the lead set illustrated. For example, atrial defibrillation and sensing electrodes might be added to either the coronary sinus lead or the right ventricular lead instead of being located on a separate atrial lead, allowing for a two-lead system.

Figure 2:
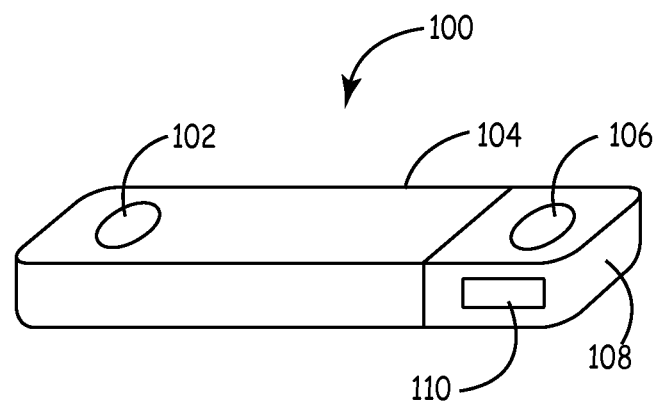
FIG. 2 is a schematic representation of another exemplary medical device in which the method and apparatus of the present application may be implemented.

FIG. 2 is a schematic representation of another exemplary medical device in which the method and apparatus of the present application may be implemented. As illustrated in FIG. 2, a medical device according to the present disclosure may take the form of a subcutaneously implantable monitoring device 100, such as a REVEAL® PLUS implantable cardiac monitor, commercially available from Medtronic Inc. of Minneapolis, Minn. Monitoring device 100 includes a hermetically sealed enclosure 104, containing the electronic circuitry used for generating cardiac pacing pulses and for monitoring the patient's heart rhythm, and a molded plastic header 108. The enclosure 104 and the header 108 each carry an electrode 102 and 106, respectively for monitoring heart rhythm. An antenna 110 may be mounted in the header 108 for use in communicating between the device and an external device, such as a programmer, for example. Monitoring device 100 may include an internal activity sensor 112, of the type typically employed in the context of rate responsive cardiac pacemakers, taking the form either of an accelerometer or a piezo-electric transducer, for example. Heart signals are detected between the electrodes 102 and 106 and measurements of physical activity are detected by sensor 112 for use in storing and calculating heart rates, heart rate trends and heart rate variability measurements, for example.

Figure 3:
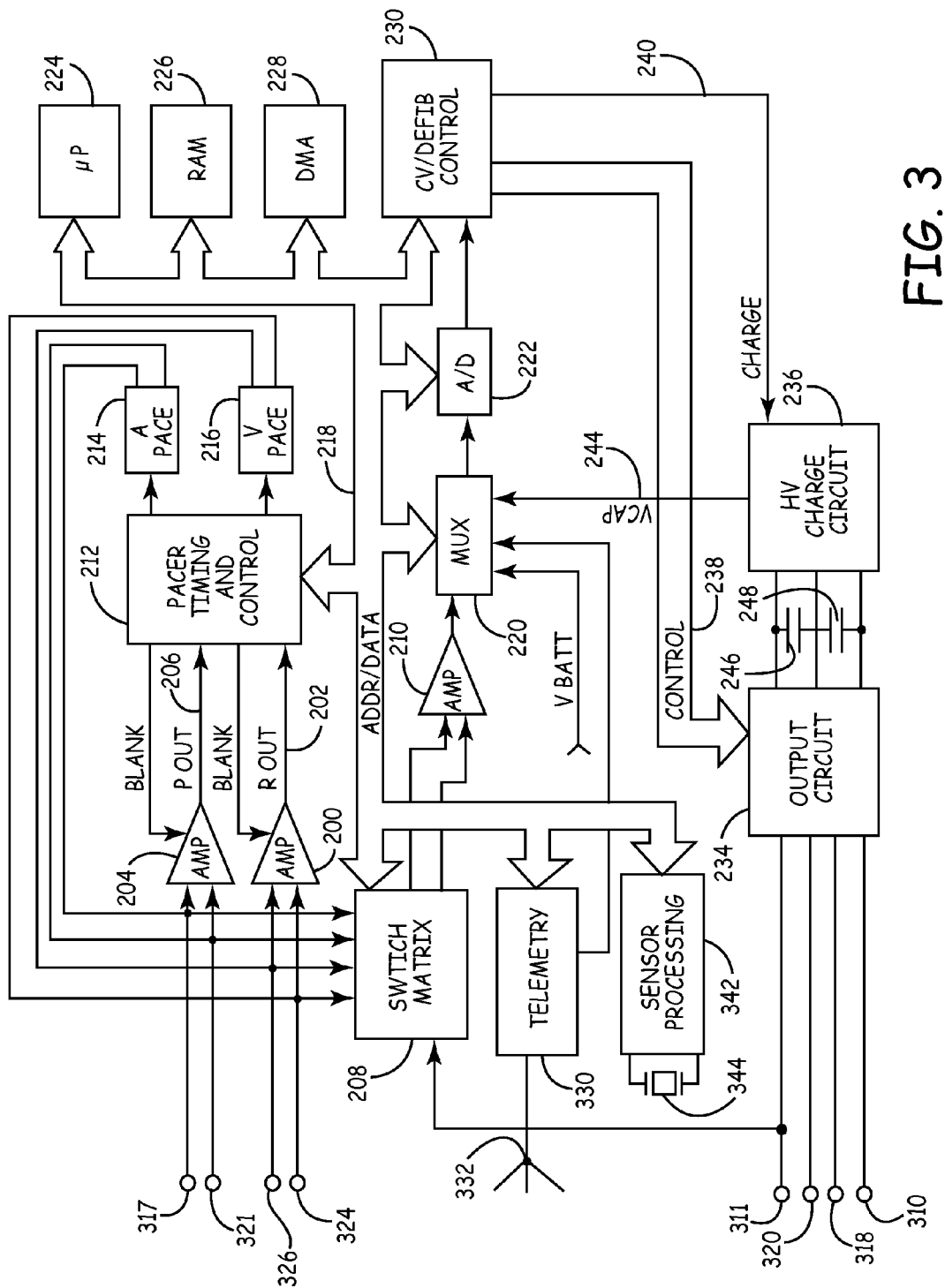
FIG. 3 is a functional schematic diagram of the medical device of FIG. 1.

FIG. 3 is a functional schematic diagram of the medical device of FIG. 1. While the medical device of FIG. 1 is shown with lead system having electrodes 8, 11, 17, 19, 20, 21, 23, 24, 26 and 28, alternate lead systems may be substituted. If the electrode configuration of FIG. 1 is employed, the correspondence to the illustrated electrodes is as follows. Electrode 311 corresponds to electrode 11, and is the uninsulated portion of the housing of the implantable pacemaker/cardioverter/defibrillator. Electrode 320 corresponds to electrode 20 and is a defibrillation electrode located in the right ventricle. Electrode 310 corresponds to electrode 8 and is a defibrillation electrode located in the coronary sinus. Electrode 318 corresponds to electrode 28 and is a defibrillation electrode located in the superior vena cava. Electrodes 324 and 326 correspond to electrodes 24 and 26, and are used for sensing and pacing in the ventricle. Finally, electrodes 317 and 321 correspond to electrodes 19 and 21 and are used for pacing and sensing in the atrium.

Electrodes 310, 311, 318 and 320 are coupled to high voltage output circuit 234. Electrodes 324 and 326 are coupled to the R-wave amplifier 200, which may take the form of an automatic gain controlled amplifier providing an adjustable sensing threshold as a function of the measured R-wave amplitude. A signal is generated on R-out line 202 whenever the signal sensed between electrodes 324 and 326 exceeds the present sensing threshold.

Electrodes 317 and 321 are coupled to the P-wave amplifier 204, which may also take the form of an automatic gain controlled amplifier providing an adjustable sensing threshold as a function of the measured R-wave amplitude. A signal is generated on P-out line 206 whenever the signal sensed between electrodes 317 and 321 exceeds the present sensing threshold. The general operation of the R-wave and P-wave amplifiers 200 and 204 may correspond to that disclosed in U.S. Pat. No. 5,117,824, by Keimel, et al., issued Jun. 2, 1992, for an Apparatus for Monitoring Electrical Physiologic Signals, incorporated herein by reference in its entirety. However, any of the numerous prior art sense amplifiers employed in implantable cardiac pacemakers, defibrillators and monitors may also usefully be employed in conjunction with the present disclosure.

Switch matrix 208 is used to select which of the available electrodes are coupled to wide band amplifier 210 for use in digital signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by ND converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal-processing methodologies known to the art.

Telemetry circuit 330 receives downlink telemetry from and sends uplink telemetry to the patient activator by means of antenna 332. Data to be uplinked to the activator and control signals for the telemetry circuit are provided by microprocessor 224 via address/data bus 218. Received telemetry is provided to microprocessor 224 via multiplexer 220. The atrial and ventricular sense amp circuits 200, 204 produce atrial and ventricular EGM signals, which also may be digitized, and uplink telemetered to an associated programmer on receipt of a suitable interrogation command. The device may also be capable of generating so-called marker codes indicative of different cardiac events that it detects. A pacemaker with marker-channel capability is described, for example, in U.S. Pat. No. 4,374,382 to Markowitz, which patent is hereby incorporated by reference herein in its entirety. The particular telemetry system employed is not critical to practicing the invention, and any of the numerous types of telemetry systems known for use in implantable devices may be used. In particular, the telemetry systems as disclosed in U.S. Pat. No. 5,292,343 issued to Blanchette et al., U.S. Pat. No. 5,314,450, issued to Thompson, U.S. Pat. No. 5,354,319, issued to Wybomy et al. U.S. Pat. No. 5,383,909, issued to Keimel, U.S. Pat. No. 5,168,871, issued to Grevious, U.S. Pat. No. 5,107,833 issued to Barsness or U.S. Pat. No. 5,324,315, issued to Grevious, all incorporated herein by reference in their entireties, are suitable for use in conjunction with the present invention. However, the telemetry systems disclosed in the various other patents cited herein which are directed to programmable implanted devices, or similar systems may also be substituted. The telemetry circuit 330 is of course also employed for communication to and from an external programmer, as is conventional in implantable anti-arrhythmia devices.

The device of FIG. 3 may additionally be provided with an activity sensor 344, mounted to the interior surface of the device housing or to the hybrid circuit within the device housing. The sensor 344 and sensor present in circuitry 342 may be employed in the conventional fashion described in U.S. Pat. No. 4,428,378 issued to Anderson et al, incorporated herein by reference in its entirety, to regulate the underlying pacing rate of the device in rate responsive pacing modes.

The remainder of the circuitry is dedicated to the provision of cardiac pacing, cardioversion and defibrillation therapies, and, for purposes of the present disclosure may correspond to circuitry known in the prior art. An exemplary apparatus is disclosed for accomplishing pacing, cardioversion and defibrillation functions as follows. The pacer timing/control circuitry 212 includes programmable digital counters which control the basic time intervals associated with DDD, VVI, DVI, VDD, AAI, DDI, DDDR, VVIR, DVIR, VDDR, AAIR, DDIR and other modes of single and dual chamber pacing well known to the art. Circuitry 212 also controls escape intervals associated with anti-tachyarrhythmia pacing in both the atrium and the ventricle, employing, any anti-tachyarrhythmia pacing therapies known to the art.

Intervals defined by pacing circuitry 212 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 224, in response to stored data in memory 226 and are communicated to the pacing circuitry 212 via address/data bus 218. Pacer circuitry 212 also determines the amplitude of the cardiac pacing pulses under control of microprocessor 224.

During pacing, the escape interval counters within pacer timing/control circuitry 212 are reset upon sensing of R-waves and P-waves as indicated by signals on lines 202 and 206, and in accordance with the selected mode of pacing on time-out trigger generation of pacing pulses by pacer output circuits 214 and 216, which are coupled to electrodes 317, 321, 324 and 326. The escape interval counters are also reset on generation of pacing pulses, and thereby control the basic timing of cardiac pacing functions, including anti-tachyarrhythmia pacing.

The durations of the intervals defined by the escape interval timers are determined by microprocessor 224, via data/address bus 218. The value of the count present in the escape interval counters when reset by sensed R-waves and P-waves may be used to measure the durations of R-R intervals, P-P intervals, PR intervals and R-P intervals, which measurements are stored in memory 226 and are used in conjunction with the present invention to measure heart rate variability and heart rate trends and in conjunction with tachyarrhythmia detection functions.

Microprocessor 224 operates as an interrupt driven device, and is responsive to interrupts from pacer timing/control circuitry 212 corresponding to the occurrences of sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts. Microprocessor 224 includes associated ROM in which the stored program controlling its operation as described below resides. A portion of the memory 226 may be configured as a plurality of recirculating buffers, capable of holding series of measured intervals, which may be analyzed in response to the occurrence of a pace or sense interrupt to determine whether the patient's heart is presently exhibiting atrial or ventricular tachyarrhythmia.

The arrhythmia detection method of the present disclosure may include any of the numerous available prior art tachyarrhythmia detection algorithms. One exemplary embodiment may employ all or a subset of the rule-based detection methods described in U.S. Pat. No. 5,545,186 issued to Olson et al. or in U.S. Pat. No. 5,755,736 issued to Gillberg et al., both incorporated herein by reference in their entireties. However, any of the various other arrhythmia detection methodologies known to the art might also be utilized.

In the event that an atrial or ventricular tachyarrhythmia is detected, and an anti-tachyarrhythmia pacing regimen is desired, timing intervals for controlling generation of anti-tachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters.

In the event that generation of a cardioversion or defibrillation pulse is required, microprocessor 224 employs the escape interval counter to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248 via charging circuit 236, under control of high voltage charging control line 240. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization. In the illustrated device, delivery of the cardioversion or defibrillation pulses is accomplished by output circuit 234, under control of control circuitry 230 via control bus 238. Output circuit 234 determines whether a monophasic or biphasic pulse is delivered, whether the housing 311 serves as cathode or anode and which electrodes are involved in delivery of the pulse.

Figure 4:
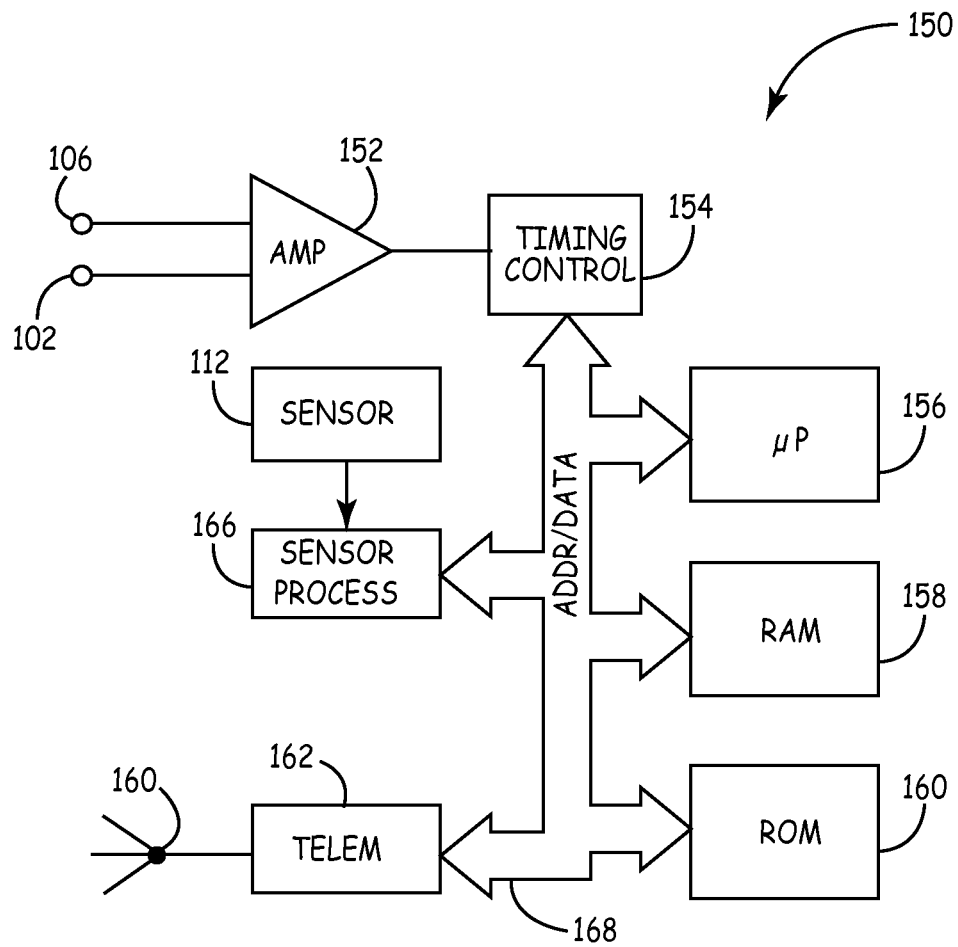
FIG. 4 is a functional schematic diagram of the medical device of FIG. 2.

FIG. 4 is a functional schematic diagram of the medical device of FIG. 2. This device consists essentially of a set of subcomponents 150 of the more complex embodiment of the device disclosed in FIG. 3. As illustrated in FIGS. 2 and 4, another exemplary medical device according to the present disclosure includes a sense amplifier 152 coupled to electrodes 102 and 106, illustrated in FIG. 2. Sense amplifier 152 may correspond to sense amplifier 204 or 200 in FIG. 3. Monitoring device 100 may be a microprocessor control device operating under control microprocessor 156 with its functionality controlled primarily by software stored in the read only memory associated therein. In this context, amplifier 152 detects the occurrence of heart depolarizations, with timing/control circuitry 154 serving to measure the durations between the detected heart depolarizations and to generate interrupts awakening microprocessor 156 so that it may store, analyze and process the detected intervals. Random Access Memory (RAM) 158 serves to store measured and calculated parameters including the calculated average heart rate values for later telemetry to an external device. Similar to the device in FIG. 3, timing and control circuitry communicates with the microprocessor and the remaining circuitry by means of the address/data bus 168. Telemetry system 162 may correspond to telemetry system 330 in FIG. 3 and, via antenna 160 transmits and receives information from the external programmer, including transmitting information with regard to the calculated median rate values and heart variability values stored in RAM 158. Sensor 112 may correspond to sensor 344 in FIG. 3 and may be a physical activity sensor as discussed above. The output of sensor 112 is passed through sensor processing circuitry 166 which may correspond to sensor processing circuitry 342 in FIG. 3.

Figure 5:
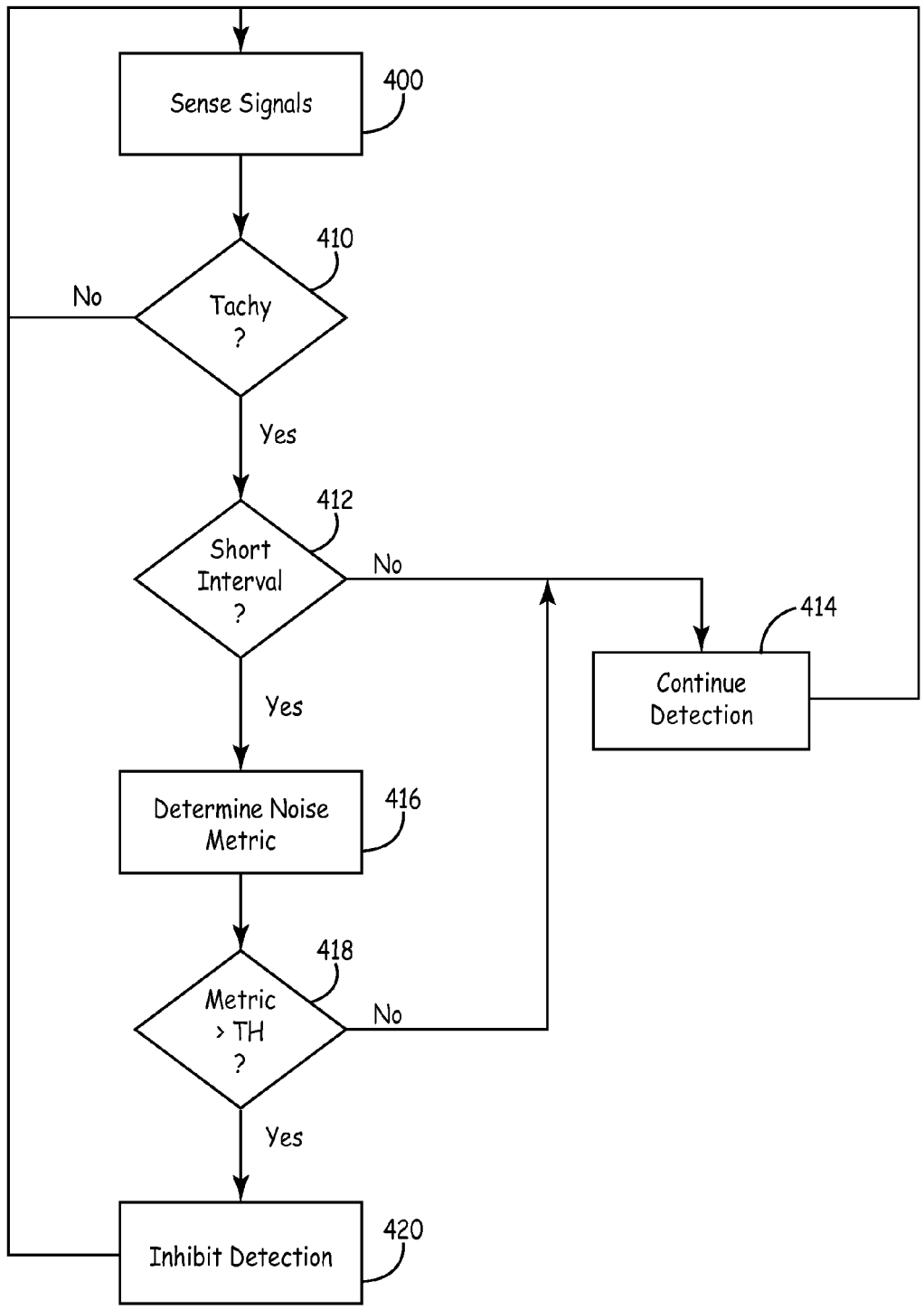
FIG. 5 is a flowchart of delivery of detection of a cardiac event in a medical device according to an embodiment of the present disclosure.
Figure 6:
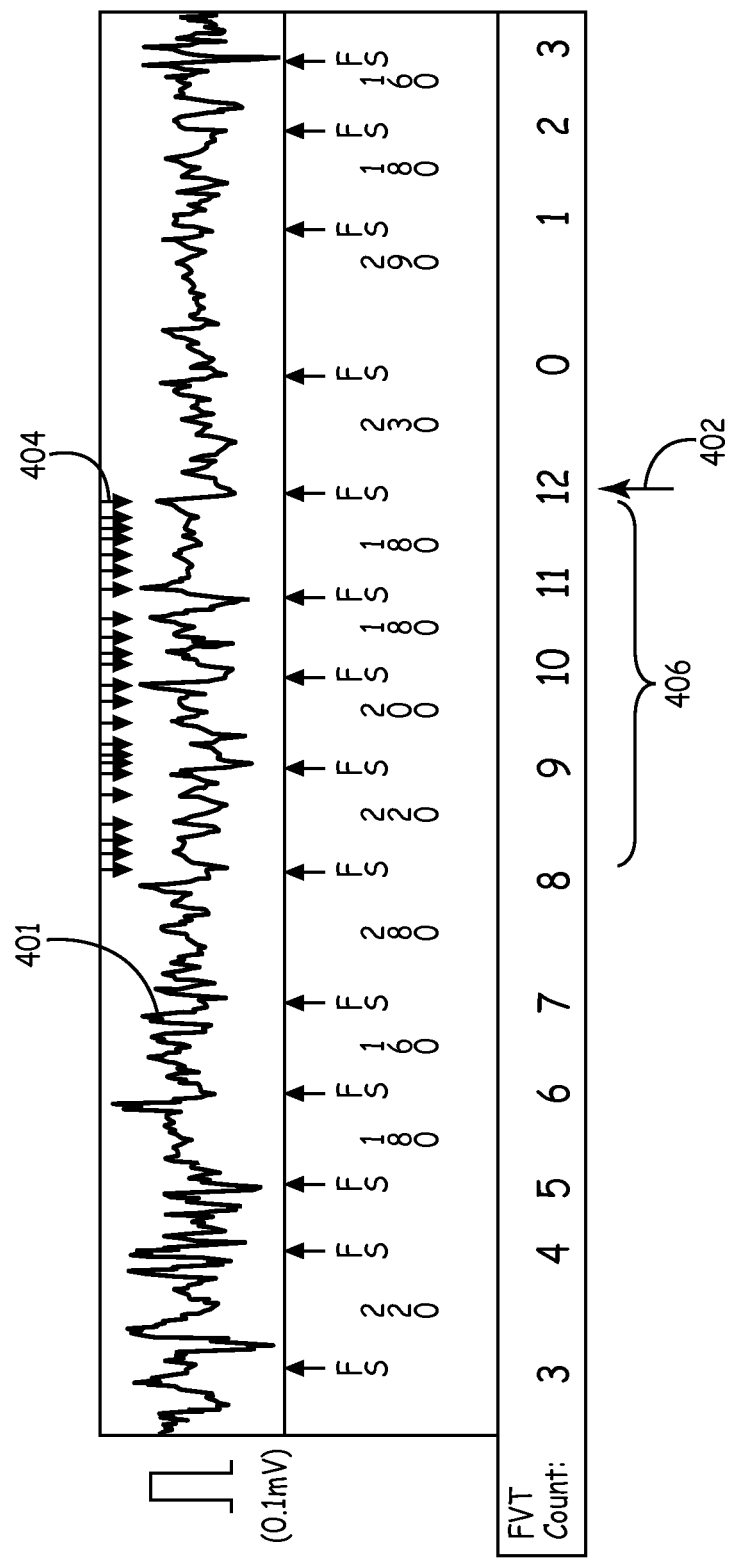
FIG. 6 is a graphical illustration of detection of a cardiac event in a medical device according to an embodiment of the present disclosure.

FIG. 5 is a flowchart of detection of a cardiac event in a medical device according to an embodiment of the present disclosure. FIG. 6 is a graphical illustration of detection of a cardiac event in a medical device according to an embodiment of the present disclosure. As illustrated in FIGS. 5 and 6, according to an embodiment of the present disclosure, during detection of cardiac events, a medical device senses one or more cardiac signals, Block 400, via electrodes, for example, and a determination is made as to whether a cardiac event requiring delivery of therapy, such as a tachycardia event, is occurring, Block 410. For example, in order to determine whether a tachycardia event is occurring, Block 410, a determination is made as to whether the number of consecutive RR intervals associated with the sensed signals that are below a predetermined detection interval, such as a tachycardia detection interval (TDI) or a fibrillation detection interval (FDI), exceeds a programmed threshold duration, known as the number of intervals to detect (NID). When the number of intervals below the predetermined detection interval exceeds the NID threshold, the tachycardia event may be occurring.

For example, as illustrated in FIG. 6, if the NID threshold is set as 12 intervals, once 12 consecutive intervals below the detection interval have occurred, 402, the NID is determined to have been met and therefore a tachycardia event is occurring, Yes in Block 410 of FIG. 5.

Since all ECGs tend to contain a certain amount of low level noise, the algorithm for detection of a cardiac event according to the present disclosure is intended to be constrained so as to be initiated only in those situations when there is an initial indication of a poor signal-to-noise ratio. If this threshold indication of poor signal-to-noise ratio is satisfied, thus ruling out the likelihood of only baseline low level noise being present, then a second noise metric is applied to determine whether the satisfaction of the detection criteria (12 consecutive intervals below the predetermined detection interval being detected) occurred as a result of oversensing, caused by noise, for example, making continued detection undesirable.

In particular, according to one embodiment, once an indication that a tachycardia event is likely occurring has been identified, as described above, Yes in Block 410, a determination is made as to whether at least one RR interval of a predetermined number of RR intervals is less than a predetermined noise interval threshold, Block 412. For example, according to one embodiment, the determination in Block 412 includes determining whether at least one RR interval of the most recent required threshold number of intervals to detect the event, i.e., one of the most recent 12 intervals, is less than the predetermined noise interval threshold. In another embodiment, the number of intervals utilized to determine the presence of a short interval, i.e., an interval less than the noise interval threshold, may be different than the number of intervals to detect the event. For example, the determination in Block 412 may include determining whether at least one RR interval out of a predetermined number of the most recent RR intervals, such as six for example, is less than the predetermined noise interval threshold.

According to one embodiment of the present disclosure, the predetermined noise interval threshold is set at 220 ms. If at least one RR interval of the predetermined number of intervals is not less than the noise interval threshold, No in Block 412, indicating the threshold indication of poor signal-to-noise ratio is not satisfied, and that therefore the likelihood that only baseline low level noise is present cannot initially be ruled out, the noise detection process is aborted and the detection process continues as scheduled, Block 414.

If at least one RR interval of the predetermined number of intervals is determined to be less than the noise interval threshold, Yes in Block 412, indicating the threshold indication of poor signal-to-noise ratio is satisfied and that therefore the likelihood that only baseline low level noise is present can be initially ruled out, a noise rejection metric is determined, Block 416.

For example, as illustrated in FIG. 6, once the NID is satisfied 402 and at least one RR interval of the predetermined number of intervals is determined to be less than 220 ms, a determination is made as to the number of signal inflections of the sensed cardiac signals 401, indicated by arrows 404, occurring over a predetermined noise metric window 406 prior to and leading up to the last RR interval associated with the NID being satisfied. It is understood that the term signal inflection refers to changes in the polarity of the slope of the ECG signal, and that according to an embodiment of the disclosure, the determination of the number of signal inflections includes determining only the number of changes from positive ECG signal slope to negative ECG signal slope, rather than determining all changes in the sign of the slope, thereby reducing the computational effort required. In addition, according to one embodiment, the predetermined noise metric window 406 is set as 0.78 seconds, although other window lengths may be utilized without departing from the scope of the present disclosure.

A determination is made as to whether the determined number of signal inflections 404 associated with the cardiac signal 401 that occur during the noise metric window 406 is greater than a noise metric threshold, Block 418. According to one embodiment, for example, the noise metric threshold may be set as being 20 inflections, so that if more than 20 signal inflections are determined to occur within the noise metric window 406, Yes in Block 418, indicating the presence of noise, detection is inhibited, Block 420, and the FVT counter and/or the VT counter are set to zero. If the determined noise metric is not greater than the noise metric threshold, No in Block 418, noise is not determined to be present and detection of cardiac events continues as scheduled, Block 414.

According to an embodiment of the disclosure, once detection is inhibited, Block 420, sensing continues so that once the VT and FVT counters have been cleared they can then begin to count up again, possibly leading to a subsequent detection, Yes in Block 410, and a subsequent inhibiting of detection, Block 420. In addition, it is understood that during inhibiting of detection in Block 420 detection may be inhibited for a predetermined period of time, such as 20 seconds, for example. In another embodiment, inhibiting detection, Block 420, may include inhibiting detection until a predetermined event has occurred, such as a determination that the noise has substantially decreased, or is no longer present. For example, detection may be inhibited until a determination that there are no longer intervals occurring that are less than the noise interval threshold over a predetermined number of intervals. According to another embodiment, detection may be inhibited until the number of signal inflections determined is reduced to be below a predetermined threshold. For example, detection may be inhibited until a determination is made that the number of signal inflections during a subsequent noise metric window is less than a predetermined inhibiting threshold, such as 15 signal inflections for example, or some other number over a predetermined number of noise metric windows It is further understood that while the determination of the noise level of the signal is described above to include determining the number of inflections in the signal, other methods for determining the noise level may be utilized.

Exemplary alternatives could include one or more of determining whether the mean frequency of the signal exceeds a predetermined frequency threshold, determining whether the number of zero crossings is greater than a zero crossing threshold, determining whether an estimate of the signal to noise ratio exceeds a predetermined threshold, or determining whether the energy level in a given high frequency band exceeds a threshold, for example.

In this way, according to the present disclosure, noise rejection is accomplished by a combination of short interval sensing and a metric of the density of ECG signal inflections (i.e., changes in the sign of the slope). A high density of signal inflections indicates that the signal contains noise. Because all ECGs will contain some low level noise (and therefore a certain density of signal inflections during quiet times), and because operations on the ECG signal require high computation demand and therefore current drain, the application of the noise rejection scheme of the present disclosure is constrained to those situations with evidence of oversensing. The evidence of oversensing is an efficient way to indicate a poor signal-to-noise ratio. In other words, the noise level must be large enough relative to the signal to cause oversensing in order to activate the noise rejection scheme.

Some of the techniques described above may be embodied as a computer-readable medium comprising instructions for a programmable processor such as the microprocessor, pacer/device timing and control circuit described above. The programmable processor may include one or more individual processors, which may act independently or in concert. A "computer-readable medium" includes but is not limited to any type of computer memory such as floppy disks, conventional hard disks, CR-ROMS, Flash ROMS, nonvolatile ROMS, RAM and a magnetic or optical storage medium. The medium may include instructions for causing a processor to perform any of the features described above for initiating a session of the escape rate variation according to the present invention.

Thus, a method and apparatus for detecting tachycardia have been presented in the foregoing description with reference to specific embodiments. It is appreciated that various modifications to the referenced embodiments may be made without departing from the scope of the disclosure as set forth in the following claims.

The invention claimed is:

1. A method of detecting a cardiac event in a medical device comprising a plurality of electrodes and a processor, the method comprising:
    sensing a cardiac signal through the plurality of electrodes;
    detecting, by the processor, RR intervals within the sensed cardiac signal;
    determining, by the processor, that the detected RR intervals include a set of consecutive RR intervals that are each less than a detection interval, the set of consecutive RR intervals being at least a predetermined number of intervals;
    after determining that the detected RR intervals include the set of consecutive RR intervals:
        determining, by the processor, whether at least one of the RR intervals in the set of consecutive RR intervals is less than an interval threshold, the interval threshold being less than the detection interval; and
        determining, by the processor, whether at least a noise metric threshold number of signal inflections occur during a predetermined noise metric window within the set of consecutive RR intervals; and
    in response to determining that at least one of the RR intervals in the set of consecutive RR intervals is less than the interval threshold and that at least the noise metric threshold number of signal inflections occur during the predetermined noise metric window:
        inhibiting, by the processor, detecting the set of consecutive RR intervals as a cardiac tachyarrhythmia, and
        inhibiting, by the processor, cardiac tachyarrhythmia detection for a period of time subsequent to inhibiting the detection of the set of consecutive RR intervals as a cardiac tachyarrhythmia.

2. The method of claim 1, wherein determining that at least a noise metric threshold number of signal inflections occur during the predetermined noise metric window includes detecting that at least a noise metric threshold number of slope changes occur during the predetermined noise metric window.

3. The method of claim 2, wherein the interval threshold corresponds to an indication of oversensing.

4. The method of claim 1, further comprising:
    aborting determining whether at least the noise metric threshold number of signal inflections occur and not inhibiting detecting in response to determining that none of the RR intervals in the set of consecutive RR intervals is less than the interval threshold; and
    not inhibiting detecting the set of consecutive RR intervals as the cardiac tachyarrhythmia in response to at least one of the RR intervals in the set of consecutive RR intervals being less than the interval threshold and less than the noise metric threshold number of signal inflections occurring during the predetermined noise metric window.

5. The method of claim 4, further comprising:
    inhibiting detection for a predetermined period of time; and
    resuming detection in response to expiration of the predetermined period of time.

6. The method of claim 4, further comprising:
    detecting that not more than an inhibiting threshold number of signal inflections has occurred during a subsequent window; and
    continuing cardiac tachyarrhythmia detection in response to detecting that not more than the inhibiting threshold number of signal inflections has occurred during the subsequent window.

7. The method of claim 6, wherein the inhibiting threshold is less than the noise metric threshold.

8. The method of claim 4, further comprising:
    determining, after inhibiting cardiac tachyarrhythmia detection, whether a predetermined number of subsequent RR intervals of the sensed cardiac signal are less than the interval threshold; and
    resuming detection in response to the subsequent RR intervals of the sensed cardiac signal not being less than the interval threshold.

9. The method of claim 1, wherein the interval threshold corresponds to an indication of oversensing.

10. A medical device comprising:
    a plurality of electrodes to sense a cardiac signal; and
    a processor configured to:
        detect RR intervals within the sensed cardiac signal,
        determine that the detected RR intervals include a set of consecutive RR intervals that are each less than a detection interval, the set of consecutive RR intervals being at least a predetermined number of intervals, after determining that the detected RR intervals include the set of consecutive RR intervals:
  determine whether at least one of the RR intervals in the set of consecutive RR intervals is less than an interval threshold, the interval threshold being less than the detection interval, and
  determine whether at least a noise metric threshold number of signal inflections occur during a predetermined noise metric window within the set of consecutive RR intervals, and
in response to determining that at least one of the RR intervals in the set of consecutive RR intervals is less than the interval threshold and that at least the noise metric threshold number of signal inflections occur during the predetermined noise metric window:
  inhibit detecting the set of consecutive RR intervals as a cardiac tachyarrhythmia, and
  inhibit cardiac tachyarrhythmia detection for a period of time subsequent to inhibiting the detection of the set of consecutive RR intervals as a cardiac tachyarrhythmia.

11. The device of claim 10, wherein determining that at least a noise metric threshold number of signal inflections occur during the predetermined noise metric window includes detecting that at least a noise metric threshold number of slope changes occur during the predetermined noise metric window.

12. The device of claim 11, wherein the interval threshold corresponds to an indication of oversensing.

13. The device of claim 10, wherein the processor is further configured to:
  abort determining whether at least the noise metric threshold number of signal inflections occur and not inhibit detecting in response to determining that none of the RR intervals in the set of consecutive RR intervals is less than the interval threshold, and
  not inhibit detecting the set of consecutive RR intervals as the cardiac tachyarrhythmia in response to at least one of the RR intervals in the set of consecutive RR intervals being less than the interval threshold and less than the noise metric threshold number of signal inflections occurring during the predetermined noise metric window.

14. The device of claim 13, wherein the processor is further configured to inhibit detection for a predetermined period of time, and resume detection in response to expiration of the predetermined period of time.

15. The device of claim 13, wherein the processor is further configured to detect that not more than an inhibiting threshold number of signal inflections has occurred during a subsequent window, and continue cardiac tachyarrhythmia detection in response to detecting that not more than the inhibiting threshold number of signal inflections has occurred during the subsequent window.

16. The device of claim 15, wherein the inhibiting threshold is less than the noise metric threshold.

17. The device of claim 13, wherein the processor is further configured to determine, after inhibiting cardiac tachyarrhythmia detection, whether a predetermined number of subsequent RR intervals of the sensed cardiac signal are less than the interval threshold, and resume detection in response to the subsequent RR intervals of the sensed cardiac signal not being less than the interval threshold.

18. The device of claim 10, wherein the interval threshold corresponds to an indication of oversensing.

19. The device of claim 10, wherein the noise metric window comprises four of the consecutive RR intervals.

20. The medical device of claim 10, wherein the set of consecutive RR intervals is a first set of consecutive RR intervals, and wherein the processor is further configured to:
  detect subsequent RR intervals within the cardiac signal,
  determine that, following the period of time subsequent to inhibiting the detection, the subsequent RR intervals include a second set of consecutive RR intervals that are each less than the detection interval, the second set of consecutive RR intervals being at least the predetermined number of intervals,
  determine that none of the RR intervals in the second set of consecutive RR intervals is less than the interval threshold, and
  deliver anti-tachyarrhythmia therapy.

21. The medical device of claim 10, wherein the set of consecutive RR intervals is a first set of consecutive RR intervals, wherein the predetermined noise metric window is a first predetermined noise metric window, and wherein the processor is further configured to:
  detect subsequent RR intervals within the cardiac signal,
  determine that, following the period of time subsequent to inhibiting the detection, the subsequent RR intervals include a second set of consecutive RR intervals that are each less than the detection interval, the second set of consecutive RR intervals being at least the predetermined number of intervals,
  determine that not more than the noise metric threshold number of signal inflections occur during a second predetermined noise metric window, and
  deliver anti-tachyarrhythmia therapy.

22. A non-transitory computer readable medium having computer executable instructions for causing a medical device to perform a method, the medical device comprising a plurality of electrodes and a processor, the method comprising:
  sensing a cardiac signal through the plurality of electrodes;
  detecting RR intervals within the sensed cardiac signal;
  determining that the detected RR intervals include a set of consecutive RR intervals that are each less than a detection interval, the set of consecutive RR intervals being at least a predetermined number of intervals;
  after determining that the detected RR intervals include the set of consecutive RR intervals:
    determining whether at least one of the RR intervals in the set of consecutive RR intervals is less than an interval threshold, the interval threshold being less than the detection interval; and
    determining whether at least a noise metric threshold number of signal inflections occur during a predetermined noise metric window within the set of consecutive RR intervals; and
  in response to determining that at least one of the RR intervals in the set of consecutive RR intervals is less than the interval threshold and that at least the noise metric threshold number of signal inflections occur during the predetermined noise metric window:
    inhibiting detecting the set of consecutive RR intervals as a cardiac tachyarrhythmia, and
    inhibiting cardiac tachyarrhythmia detection for a period of time subsequent to inhibiting the detection of the set of consecutive RR intervals as a cardiac tachyarrhythmia.

* * * * *